US009566274B2

(12) United States Patent
Fatmi et al.

(10) Patent No.: US 9,566,274 B2
(45) Date of Patent: *Feb. 14, 2017

(54) METHODS FOR ENHANCING THE RELEASE AND ABSORPTION OF WATER INSOLUBLE ACTIVE AGENTS (71) Applicant: BANNER LIFE SCIENCES LLC, High Point, NC (US)

(72) Inventors: Aqeel A. Fatmi, High Point, NC (US); Tae Kyoung Kim, Seongnam (KR); Karla E. Madrigal, Sandy, UT (US)

(73) Assignee: Banner Life Sciences LLC, High Point, NC (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/559,619

(22) Filed: Dec. 3, 2014

(65) Prior Publication Data

US 2015/0182519 A1    Jul. 2, 2015

Related U.S. Application Data

(63) Continuation of application No. 13/956,571, filed on Aug. 1, 2013, now Pat. No. 8,920,844, which is a
(Continued)

(51) Int. Cl.
*A61K 9/14* (2006.01)
*A61K 31/4709* (2006.01)
(Continued)

(52) U.S. Cl.
CPC ............ *A61K 31/4709* (2013.01); *A61K 9/14* (2013.01); *A61K 9/145* (2013.01); *A61K 9/167* (2013.01);
(Continued)

(58) Field of Classification Search
None
See application file for complete search history.

(56) References Cited

U.S. PATENT DOCUMENTS

| 4,880,634 A | 11/1989 | Speiser |
| 5,145,684 A | 9/1992 | Liversidge |
| (Continued) | | |

FOREIGN PATENT DOCUMENTS

| EP | 0212875 | 7/1986 |
| JP | 54122719 | 9/1979 |
| (Continued) | | |

OTHER PUBLICATIONS

Bodmeier, et al., "Process and Formulation Variables in the Preparation of Wax Microparticles by a Melt Dispersion Technique. I. Oil-in-water Technique for Water-insoluble Drugs", J. Microencapsulation, 9(1):89-98 (1992).
(Continued)

*Primary Examiner* — Isaac Shomer
(74) *Attorney, Agent, or Firm* — Brinks Gilson & Lione (57) ABSTRACT

Methods for enhancing the release and/or absorption of poorly water soluble active agents are described herein. The method involves dissolving, melting, or suspending a poorly water soluble active agent in one or more molten fatty acids, conjugated fatty acids, (semi-) solid surfactants of high HLB value, and/or hydrophilic polymers. The molten active agent mixture is then suspended and homogenized in a hydrophilic or lipophilic carrier to form microparticles suspended in the hydrophilic or lipophilic carrier. The particles suspended in the hydrophilic or lipophilic carrier can be encapsulated in a hard or soft gelatin or non-gelatin capsule. It is believed that the microparticles produced by the method described above will exhibit enhanced dissolution profiles. In vitro release studies of formulations containing cilostazol and fenofibrate showed 100% dissolution of cilostazol in 15
(Continued)

minutes and over 90% dissolution of fenofibrate in 35 minutes.

21 Claims, 7 Drawing Sheets

Related U.S. Application Data continuation of application No. 12/638,212, filed on Dec. 15, 2009, now Pat. No. 8,524,280.

(60) Provisional application No. 61/122,497, filed on Dec. 15, 2008.

(51) Int. Cl.
  *A61K 9/50*   (2006.01)
  *A61K 47/12*   (2006.01)
  *A61K 31/235*   (2006.01)
  *A61K 47/44*   (2006.01)
  *A61K 31/216*   (2006.01)
  *A61K 9/16*   (2006.01)
  *A61K 9/48*   (2006.01)
  *A61K 47/14*   (2006.01)

(52) U.S. Cl.
  CPC ............... *A61K 9/1682* (2013.01); *A61K 9/50* (2013.01); *A61K 9/5015* (2013.01); *A61K 9/5089* (2013.01); *A61K 31/216* (2013.01); *A61K 31/235* (2013.01); *A61K 47/12* (2013.01); *A61K 47/44* (2013.01); *A61K 9/16* (2013.01); *A61K 9/1658* (2013.01); *A61K 9/48* (2013.01); *A61K 47/14* (2013.01)

(56) References Cited

U.S. PATENT DOCUMENTS

| | | | |
|---|---|---|---|
| 5,545,628 A | 8/1996 | Deboeck | |
| 5,885,486 A * | 3/1999 | Westesen | A01N 25/04 428/402.24 |
| 6,197,349 B1 | 3/2001 | Westesen | |
| 6,277,405 B1 | 8/2001 | Stamm | |
| 6,375,986 B1 | 4/2002 | Ryde | |
| 6,511,681 B2 | 1/2003 | Vladyka, Jr. | |
| 6,534,088 B2 | 3/2003 | Guivarch | |
| 6,652,881 B2 | 11/2003 | Stamm | |
| 8,524,280 B2 * | 9/2013 | Fatmi | A61K 9/5015 424/452 |
| 8,920,844 B2 * | 12/2014 | Fatmi | A61K 9/5015 424/489 |
| 2002/0009496 A1 | 1/2002 | Stamm | |
| 2005/0048126 A1 | 3/2005 | Rabinow | |
| 2005/0249799 A1 | 11/2005 | Jacob | |
| 2006/0105050 A1 | 5/2006 | Holm | |
| 2006/0110444 A1 | 5/2006 | Holm | |
| 2006/0141052 A1 * | 6/2006 | Lerner | A61K 9/167 424/489 |
| 2006/0188529 A1 | 8/2006 | Bobotas | |
| 2006/0222707 A1 * | 10/2006 | Lerner | A61K 9/2013 424/464 |

FOREIGN PATENT DOCUMENTS

| | | |
|---|---|---|
| JP | 6019981 | 10/1985 |
| WO | 9525504 | 9/1995 |
| WO | 9811881 | 3/1998 |
| WO | 01214454 | 3/2001 |
| WO | 2004030658 | 4/2004 |
| WO | 2005034920 | 4/2005 |
| WO | 2005065652 | 7/2005 |
| WO | 2006062933 | 6/2006 |

OTHER PUBLICATIONS

Hanafy, et al., "Pharmacokinetic evaluation of oral fenofibrate nansuspensions and SLN in comparison to conventional suspensions of micronized drug", Advanced Drug Delivery Reviews, 59(6):419-426 (2007).
Kasim, et al, "Molecular Properties of Who Essential Drugs and Provisional Biopharmaceutical Classification," Mot. Pharm., 1(1): 85-96 (2004).
Keck, et al., "Lipid nanoparticles for encapsulation of actives: dermal and oral formulations", Am. Pharmaceutical Rev., 10(6):78-82 (2007).
Kumar, et al., "Development and evaluation of nitrendipine loaded solid lipid nanoparticles: Influence of wax and glyceride lipids on plasma pharmacokinetics", Int. J Pharm., 335:167-75 (2007).
Muhlen, et al., "Solid lipid nanoparticles (SLN) for controlled drug delivery—Drug release and release mechanism", Eu J Pharm. Biopharm., 45:149-55 (1998).
Muller, et al., "Solid lipid nanoparticles (SLN) for controlled drug delivery—a review of the state of the art", Eu J Pharm Biopharm., 50:161-77 (2000).
Reithmeier, et al., "Development and characterization of lipid microparticles as a drug carrier for somatostatin", Int. J. Pharmaceutics, 218:133-143 (2001).
Zur Muehlen, et al., "Solid lipid nanoparticles (SLN) for controlled drug delivery" Drug release and release mechanism, European J. Pharmaceutics and Biopharmaceutics, 45 (2):149-155 (1998).
International Search Report, PCT/US2009/068017, mailed Apr. 29, 2011.

* cited by examiner

METHODS FOR ENHANCING THE RELEASE AND ABSORPTION OF WATER INSOLUBLE ACTIVE AGENTS

CROSS REFERENCE TO RELATED APPLICATIONS

The present application is a continuation of pending U.S. application Ser. No. 13/956,571, filed Aug. 1, 2013, which is a continuation of pending U.S. application Ser. No. 12/638,212, filed Dec. 15, 2009, which is related to and claims priority to U.S. Ser. No. 61/122,497 entitled "Methods for Enhancing the Release and Absorption of Water Insoluble Active Agents" by Aqeel Fatmi, Tae Kyoung Kim, and Karla Madrigal, filed Dec. 15, 2008, all of which are herein incorporated by reference in their entirety

FIELD OF THE INVENTION

This invention is generally in the field of methods of manufacture of microparticles with enhanced release and absorption of water-insoluble active agents.

BACKGROUND OF THE INVENTION

Formulation of poorly water soluble active agents, particularly in liquid and semi-solid forms, is a challenging task due to incompatibility between the carrier and the fill material. This incompatibility can result in agglomerization of the active agent over time which can result in low in vitro/in vivo dissolution. Further, active agents which have low solubility in water and/or low absorption in vivo (classified as BCS Class II and Class IV active agents under the Biopharmaceutical Classification System) can be difficult to integrate into a formulation due to the uncertainty surrounding the correlation between in vitro and in vivo performance. For example, BCS Class II and Class IV active agents can exhibit significant food effects, particularly with high fat meals.

Different techniques for enhancing the solubility and bioavailability of water soluble active agents have been described in the literature. U.S. Pat. No. 5,145,684 to Liversidge et al. describes dispersible particles containing a crystalline active agent substance having a surface modifier adsorbed on the surface thereof. The particles are made by wet milling in the presence of grinding media in conjunction with a surface modifier. Liversidge does not disclose or suggest making microparticles by melting or dissolving a water-insoluble active agent in a coating material and adding the mixture to a hydrophilic or lipophilic carrier to form microparticles.

U.S. Pat. No. 6,652,881 to Stamm et al. describes compositions containing micronized fenofibrate, wherein the compositions have a dissolution of at least 10% in 5 minutes, 20% in 10 minutes, 50% in 20 minutes, and 75% in 30 minutes as measured using the rotating blade at 75 rpm according to the European Pharmacopoeia, in a dissolution medium constituted by water with 2% by weight polysorbate 80 or 0.025 M sodium lauryl sulfate. The compositions contain an inert hydrosoluble carrier covered with at least one layer containing a fenofibrate active ingredient in a micronized form, a hydrophilic polymer, and optionally a surfactant; and optionally one or several outer phase(s) or layer(s). Stamm does not disclose or suggest making microparticles by melting or dissolving a water-insoluble active agent in a coating material and adding the mixture to a hydrophilic or lipophilic carrier to form microparticles.

U.S. Pat. No. 6,375,986 to Ryde et al. describes solid dose nanoparticulate compositions comprising a poorly soluble active agent, at least one polymeric surface stabilizer, and dioctyl sodium sulfosuccinate (DOSS). The polymeric surface stabilizer is adsorbed on the surface of the active agent in an amount sufficient to maintain an effective average particle size of less than about 1 micron. Ryde does not disclose or suggest making microparticles by melting or dissolving a water-insoluble active agent in a coating material and adding the mixture to a hydrophilic or lipophilic carrier to form microparticles.

U.S. Pat. No. 5,545,628 to Deboeck et al. describes a pharmaceutical composition for treating hyperlipidemia or hypercholesterolemia or both in a mammal, which contains an effective amount of each of fenofibrate and an excipient containing one or more polyglycolyzed glycerides. The compositions are prepared by co-melting the fenofibrate and the polyglycolyzed glycerides to form a homogeneous mixture or solution. The molten mixture can be filled into hard gelatin capsules. Deboeck does not disclose or suggest making microparticles by melting or dissolving a water-insoluble active agent in a coating material and adding the mixture to a hydrophilic or lipophilic carrier to form microparticles.

WO 2006/062933 to Reliant Pharmaceuticals, Inc. describes fenofibrate compositions containing fenofibrate solubilized in fatty acid esters. The acid portion or the ester portion of the fatty acid is a $C_1$-$C_{15}$ group, preferably a $C_1$-$C_6$, more preferably a $C_1$-$C_4$ group. The fenofibrate may be dissolved in the fatty acid esters with or without the use of heat, preferably without heating. The '933 application does not disclose or suggest making microparticles by melting or dissolving a water-insoluble active agent in a coating material and adding the mixture to a hydrophilic or lipophilic carrier to form microparticles.

There exists a need for additional methods for enhancing the solubility and bioavailability of water-insoluble active agents.

Therefore, it is an object of the invention to provide methods for enhancing the solubility and bioavailability of water-insoluble active agents.

It is further an object of the invention to provide compositions which exhibit enhanced solubility and bioavailability of water-insoluble active agents and methods of using thereof.

SUMMARY OF THE INVENTION

Methods for enhancing the in vivo release and absorption of poorly water soluble active agents are described herein. The method involves dissolving, melting, or suspending a poorly water soluble active agent in one or more fatty acids, conjugated fatty acids, (semi-) solid surfactants having a high HLB value, and/or hydrophilic polymers. Suitable fatty acids include $C_{10}$-$C_{18}$ fatty acids, preferably $C_{16}$-$C_{18}$ fatty acids. Suitable conjugated fatty acids include $C_{10}$-$C_{18}$ fatty acids, preferably $C_{16}$-$C_{18}$ fatty acids, conjugated with glycerol (e.g., monoglycerides), monosaccharides, and/or polyethylene glycol (PEG). Suitable hydrophilic polymers include poloxomers and poloxamines.

The active agent mixture is suspended and homogenized in a hydrophilic or lipophilic phase to form microparticles suspended in the hydrophilic or lipophilic phase. The hydrophilic or lipophilic phase can act as a secondary rate controlling barrier which modifies the rate of release of the active agent. The particles suspended in the hydrophilic or lipophilic phase can be formulated in an oral dosage form.

For example, the microparticles dispersed in the hydrophilic or lipophilic carrier can be encapsulated in a hard or soft gelatin or non-gelatin capsule.

The particle size of the final formulation is determined by the homogenization process, particularly the homogenization time. Typical particles sizes are between 50 nm and 25 microns. In one embodiment, the diameter of the particles is from about 0.1 to about 25 microns, preferably from about 10 to about 25 microns, more preferably from about 10 to about 20 microns. In another embodiment, the microparticles have a diameter less than 10 microns, less than 5 microns, less than 1 micron, less than 0.5 microns, less than 0.25 microns, or less than 0.1 micron. The microparticles may be spherical or any other shape.

The microparticles produced by the method described herein can exhibit enhanced dissolution profiles. In vitro release studies of formulations containing cilostazol and fenofibrate showed 100% dissolution of cilostazol in 15 minutes and over 90% dissolution of fenofibrate in 35 minutes. Further, fatty acid-coated cilostazol nanoparticles exhibited enhanced absorption in vivo compared to Pletal® (cilostazol in tablet form, suspended in water) and cilostazol suspended in an oil-based carrier containing lecithin and Capmul (CLZ-02).

DETAILED DESCRIPTION OF THE INVENTION

I. Definitions

"Water-insoluble active agent", as used herein, refers to an active agent which does not dissolve in water and/or does not form a homogenous single phase with water. For example, the active agent may have a solubility in water less than 10 mg/ml at 25° C., less than 5 mg/ml at 25° C., less than 1 mg/ml at 25° C., or less than 0.5 mg/ml at 25° C.

"Lipophilic carrier", as used herein, refers to a material or materials that have an affinity for lipids.

"Hydrophilic carrier", as used herein, refers to a material or materials having an affinity for water.

"Semi-solid", as used herein, refers to a material or materials having the attributes of both a solid and a liquid, for example, having the rigidity and viscosity intermediate between a solid and a liquid.

"Microparticles", as used herein, generally refers to a particle of a relatively small size, but not necessarily in the micron size range; the term is used in reference to particles of sizes that can be, for example, less than about 50 nm to about 100 microns or greater. In one embodiment, the diameter of the particles is from about 0.1 to about 25 microns, preferably from about 10 to about 25 microns, more preferably from about 10 to about 20 microns. In another embodiment, the diameter of the particles is less than 10 microns, less than 5 microns, less than 1 micron, less than 0.5 microns, less than 0.25, or less than 0.1 microns. As used herein, the term microparticle encompasses microspheres, microcapsules, microparticles, and nanoparticles unless specified otherwise. The microparticle may be of composite construction and is not necessarily a pure substance. The microparticles may be spherical or any other shape.

"Poor absorption", as used herein, refers to a drug which has limited absorption in the gastrointestinal tract. Drugs having poor absorption in the gastrointestinal tract generally have low aqueous solubility, e.g., less than 10 mg/ml at 25° C.

"High permeability", as used herein, refers to drugs wherein the extent of absorption in humans is determined to be >90% of an administered dose, based on mass-balance or in comparison to an intravenous reference dose.

"High hydrophile-lipophile balance" or "high HLB", as used herein, generally refers to a material or materials having an HLB of greater than about 10, preferably greater than 16.

"Surfactant", as used herein, refers to amphiphilic compounds, that is, compounds containing both hydrophilic and hydrophobic groups. Surfactants can be classified by their hydrophile-lipophile balance (HLB). Surfactants with lower HLB value are more lipophilic, while surfactants with a higher HLB value are more hydrophilic.

"$AUC_{0-24}$", as used herein, refers to the area under the plasma concentration curve from time zero to 24 hours. The $AUC_{0-24}$ is calculated using the linear trapezoidal rule.

II. Methods of Making Microparticles

Methods of making microparticles containing one or more water-insoluble active agents are described herein. The microparticles contain the active agent coated with, dissolved in, or dispersed in one or more coating materials. Exemplary coating materials include fatty acids, conjugated fatty acids, surfactants having a high HLB, hydrophilic polymers, and combinations thereof. The microparticles can exhibit relatively rapid dissolution and enhanced absorption of the active agent compared to the active agents suspended in an aqueous or oil-based carrier.

A. Active Agents

Any therapeutic, prophylactic, or diagnostic agent, nutraceutical, or other agent (collectively referred to as "active agents") can be incorporated into the microparticles. The active agent typically has a low solubility in water and/or poor absorption in vivo. In one embodiment, the active agent is an active agent having high permeability and low solubility in vivo or an active agent having low permeability and low solubility in vivo. Under the Biopharmaceutics Classification System, such active agents are characterized as Class II and IV active agents, respectively.

Suitable classes of active agents include, but are not limited to, analgesics, anti-inflammatory agents, antihelmintics, anti-arrhythmic agents, antibacterials, anticoagulants, antidepressants, antidiabetics, antiepileptics, antimalarials, antimigrane agents, antihistamines, antihypertensives, antimuscarinic agents, antimycobacterial agents, antineoplastic agents, immunosuppressants agents, antiprotozoal agents, antithyroid agents, antiviral agents, anxiolytic sedatives, astringents, beta adrenoceptor blocking agent, blood products and substitutes, cardiac ionotropic agents, corticosteroids, cough suppressants, diagnostic agents, diuretics, dopaminergics, haemostatics, lipid regulating agents, muscle relaxants, parasympathomimetics, prostaglandins, sex hormones, stimulants and anoretics, sympathomimetics, thyroid agents, and vasodilators.

Examples of Class II and Class IV active agents are described in Amidon et al., *Mol. Pharm.*, Vol. 1, No. 1, 85-96 (2004)). Examples of Class II and Class IV active agents include, but are not limited to, fenofibrate, cilostazol, acetazolamide, albendazole, allopurinol, azothioprine, carbamazepine, clofazimine, dapsone, diazepam, diloxanide furoate, doxycycline, efavirenz, furosemide, glibenclamide, griseofulvin, haloperidol, ibuprofen, lopinavir, nevirapine, niclosamide, nifedipine, paracetamol, parathyroid calcitonin, retinol palmitate, ritonavir, sulfadiazine, sulfamethoxazole, and sulfasalazine.

The concentration range of the active agent is up to about 50%, preferably about 1 to about 30%, more preferably from about 1 to about 15% by weight of the composition containing the microparticles and carrier. Alternatively, the percent loading of the drug in the microparticles is from about 1% to about 50%, from about 1% to about 40%, from about 1% to about 30%, from about 1% to about 25%, or from about 1% to about 20%.

In one embodiment, the active agent is a fibrate, such as fenofibrate. As used herein the term "fibrate" means any of the fibric acid derivatives useful in the methods described herein, e.g., fenofibrate. Fenofibrate is a fibrate compound, other examples of which are bezafibrate, beclobrate, binifibrate, ciplofibrate, clinofibrate, clofibrate, clofibric acid, etofibrate, gemfibrozil, nicofibrate, pirifibrate, ronifibrate, simflbrate, and theofibrate.

Generally, fibrates are used to treat conditions such as hypercholesterolemia, mixed lipidemia, hypertriglyceridemia, coronary heart disease, and peripheral vascular disease (including symptomatic carotid artery disease), and prevention of pancreatitis. Fenofibrate may also help prevent the development of pancreatitis (inflammation of the pancreas) caused by high levels of triglycerides in the blood. Fibrates are also known to be useful in treating renal failure. Fibrates may also be used for other indications where lipid regulating agents are typically used.

As used herein the term "fenofibrate" is used to mean fenofibrate (2-[4-(4-chlorobenzoyl)phenoxy]-2-methyl-propanoic acid, 1-methylethyl ester) or a salt thereof. Fenofibrate is used to lower triglyceride (fat-like substances) levels in the blood. Specifically, fenofibrate reduces elevated LDL-C, Total-C, triglycerides, and Apo-B and increases HDL-C. The drug has also been approved as adjunctive therapy for the treatment of hypertriglyceridemia, a disorder characterized by elevated levels of very low density lipoprotein (VLDL) in the plasma.

The absolute bioavailability of conventional microcrystalline fenofibrate cannot be determined as the compound is virtually insoluble in aqueous media suitable for injection. However, fenofibrate is well absorbed from the gastrointestinal tract.

In another embodiment, the active agent is cilastazol. Cilostazol is a selective PDE3 phosphodiesterase inhibitor with therapeutic focus on cAMP. It inhibits platelet aggregation and is a direct arterial vasodilator. Its main effects are dilation of the arteries supplying blood to the legs and decreasing platelet coagulation.

B. Coating Materials

The water-insoluble active agent is coated with one or more coating materials. Exemplary coating materials include fatty acids, conjugated fatty acids, surfactants having a high HLB, hydrophilic polymers, and combinations thereof. The coating materials are preferably not phospholipids.

1. Fatty Acids and Esters of Fatty Acids

Suitable fatty acids include $C_{10}$-$C_{18}$ fatty acids, more preferably $C_{16}$-$C_{18}$ fatty acids. Exemplary fatty acids include, but are not limited to, dodecanoic (lauric) acid, tetradecanoic (myristic) acid, hexadecanoic (palmitic) acid, heptadecanoic (margaric) acid, octadecanoic (stearic) acid, eicosanoic (arachidic) acid, docosanoic (behenic) acid, tetracosanoic (lignoceric) acid, hexacosanoic (cerotic) acid, heptacosanoic (carboceric) acid, octacosanoic (montanic) acid, triacontanoic (melissic) acid, dotriacontanoic (lacceroic) acid, tritriacontanoic (ceromelissic) acid, tetratriacontanoic (geddic) acid, and pentatriacontanoic (ceroplastic) acid. The fatty acids can be saturated fatty acids, monounsaturated fatty acids, polyunsaturated fatty acid, or combinations thereof.

Oils, for example, vegetable oils, such as soybean oil can be used alone or in combination with the coating materials listed above. Soybean oil contains 14.4% saturated fatty acids, 23.3% monounsaturated fatty acids, such as oleic acid, and 57.9% polyunsaturated fatty acids, such as linoleic acid and alpha linoleic acid.

In one embodiment, the fatty acid is covalently coupled to glycerol, a monosaccharide, such as sorbitol or sorbitan, a polyalkylene oxide, such as polyethylene glycol and polypropylene glycol, or combinations thereof. These materials are referred to as conjugated fatty acids. Suitable conjugated fatty acids include, but are not limited to, polyethylene glycol esters of fatty acids, such as those available commercially under the tradename Gelucire®, sorbitan esters of fatty acids, such as sorbitan monostearate, glycerol fatty acid esters of the fatty acids listed above, such as glycerol behenate and glyceryl monostearate, and combinations thereof.

The concentration range of the fatty acid is from about 1 to about 20% by weight of the composition, preferably from about 5 to about 15% by weight of the composition (microparticles and carrier).

2. Surfactants Having High HLB

The water-insoluble active agent can be coated with one or more surfactants, alone or in combination with or more fatty acids or conjugated fatty acids and/or one or more hydrophilic polymers. In one embodiment, the surfactant has an HLB value greater than about 10, greater than about 12, greater than about 14, or greater than about 16 (on a scale of 1-18). Surfactants having the desired HLB are known in the art. The surfactant can be anionic, cationic, or non-ionic. In one embodiment, the surfactant is a non-ionic surfactant.

Examples of such surfactants include, but are not limited to, polysorbate 20, 40, and 80 (marketed under the name TWEEN®), polyoxyethylene monostearate, some sugar esters, such as sucrose monolaurate, ethoxylated nonyl phenols, alpha olefin sulfonates, ethoxylated tallow amines, ethylene oxide/propylene oxide block copolymers, ethoxylated soya amines, fatty acids and alcohols, polyethoxylated castor oil, polysorbates, polyoxyethylene alkyl ethers, and polyoxyethylene stearates.

In one embodiment, the surfactant is a high HLB surfactant containing a fatty acid chain. Suitable surfactants include, but are not limited to, polyethoxylated castor oil, polysorbates, polyoxyethylene alkyl ethers, and polyoxyethylene stearates.

Polyoxyethylene castor oil derivatives contain mainly ricinoleyl glycerol ethoxylated with 30-50 molecules of ethylene oxide. Polysorbates or polyoxyethylene sorbitan fatty acid esters are a series of partial fatty acids esters of sorbitol and its anhydrides copolymerized with approximately 20, 5, or 4 moles of ethylene oxide for each mole of sorbitol and its anhydrides. The resulting product is a mixture of molecules having a wide range of molecular weights. Polyoxyethylene alkyl ethers are a series of polyoxyethylene glycol ethers of linear fatty alcohols (n-alcohols), such as lauryl, myristyl, cetyl, and stearyl alcohol. Polyoxyethylene stearates are produced by polyethoxylation of stearic acid.

Without desiring to be bound by any theory, it is believed that the hydrophilic part of the surfactant enhances the compatibility of the active agent with the aqueous dissolution media in vitro or in vivo and that the fatty acid side chain enhances absorption via fatty acid oxidation. During fatty acid oxidation, intracellular $Ca^{2+}$ is consumed which results in the widening of gap junctions, allowing passage of the active agent between cells. Further, such coated particles may be more stable than drug alone, for example, by preventing oxidation of the active agent.

The concentration of the surfactant is from about 1 to about 50%, preferably from about 5 to about 15% by weight of the composition (microparticles and carrier).

3. Hydrophilic Polymers

Suitable hydrophilic polymers include, but are not limited to, poloxamers, poloxamines, polyethylene glycols, polyvinyl alcohols, polyvinylpyrrolidone, poly(vinyl alcohol), cellulosic materials, such as hydroxypropylcellulose, hydroxymethylcellulose, hydroxypropylmethyl-cellulose, gelatin, carboxymethyl cellulose, and polypeptides.

The concentration of the hydrophilic polymer is from about 1 to about 50% by weight of the composition, more preferably from about 5 to about 15% by weight of the composition. If the hydrophilic polymer is a polyethylene glycol, the concentration is from about 1 to about 80% by weight of the composition, from about 30 to about 60%, from about 35% to about 60%, or from about 40% to about 60% by weight of the composition (microparticles and carrier).

C. Carrier Materials

In one embodiment, the microparticles are formed by adding a mixture of the drug and coating material(s) to a pharmaceutically acceptable carrier. In one embodiment, the carrier is a hydrophilic or lipophilic carrier. The resulting particles are suspended in the carrier. The carrier may be a single component or a mixture of components. The carrier can include solvents, surfactants, or other excipients. The carrier materials can alter or modify the rate of release of the drug from the microparticles and/or the rate of dissolution of the drug. The compositions may exhibit a biphasic release profile due to the controlled release properties of the microparticles and the controlled release properties of the carrier. Varying the qualitative and quantitative composition of the carrier materials may allow one to modulate the release profile of the active agent. The carrier may contain one or more rate controlling excipients which regulate release of the active agent. Exemplary rate controlling excipients include, but are not limited to, glyceryl behenate, GELUCIRE®, Cremophor, hydrogenated vegetable oil, bees wax, cellulosic polymers such as hypromellose, alginates, CARBOPOL® and combinations thereof.

In one embodiment, the carrier is a hydrophilic carrier containing a surfactant having a HLB value greater than about 10, greater than about 12, greater than about 14, or greater than about 16, and/or is water soluble. Exemplary hydrophilic carriers include, but are not limited to, polyethylene glycols, polyoxyethylene 32 lauric glycerides (available from Abitech under the tradename ACCONON® M-44), polyoxyethylene 8 caprylic/capric glycerides (available from Abitech under the tradename ACCONON® MC-8) and glycofurol. The hydrophilic vehicle can further contain one or more miscible solvents such as glycerin, ethanol, glycofurol, and caprylocaproyl macrogol-8 (available from Gattefosse S.A., Saint Priest, France under the tradename LABRASOL®).

In one embodiment, the hydrophilic carrier is water or an alcohol. In another embodiment, the carrier is a hydrophilic carrier mixture containing polyethylene glycol, and optionally one or more surfactants and/or water. In a particular embodiment, the hydrophilic carrier is a mixture of PEG 400 (e.g., 57% by weight of the composition), water (e.g., 8% by weight of the composition), and Tween 20 (e.g., 10% by weight of the composition). The hydrophilic carrier can also contain Cremophor RH 40. The concentration of the hydrophilic carrier is generally from about 50% to about 85% by weight of the composition (microparticles and carrier), preferably from about 70 to about 80% by weight of the composition.

In another embodiment, the carrier is a lipophilic carrier. In a preferred embodiment, the lipophilic carrier has an HLB value of less than about 10 and/or is oil soluble. Exemplary lipophilic oily vehicles include, but are not limited to, vegetable oils, medium chain mono-, di-, and triglycerides, glyceryl stearates (available from Sasol under the tradename IMWITOR®), polyoxyethylated oleic glycerides (available from Gattefosse, S.A., Saint Priest, France, under the trandename LABRAFIL®), mineral oil, mono- and diglyceride emulsifiers such as glyceryl monooleate, glyceryl monocaprate, glyceryl monocaprylate, propylene glycol monocaprylate, and propylene glycol monolaurate (available from Abitec Corp., Columbus, Ohio, under the tradename CAPMUL®), and dimethylpolysiloxanes such as simethicone.

The concentration of the lipophilic carrier is generally from about 10% to about 50% by weight of the composition (microparticles and carrier), preferably from about 5 to about 35% by weight of the composition.

D. Other Additives

The compositions described can contain one or more pharmaceutically acceptable excipients that are considered safe and effective and may be administered to an individual without causing undesirable biological side effects or unwanted interactions. Exemplary additives include, but are not limited to, solvents, suspending agents, dispersants, buffers, pH modifying agents, isotonicity modifying agents, preservatives, antimicrobial agents, and combinations thereof.

Suitable additives for inclusion in the compositions described herein include, but are not limited to, antioxidants (e.g., alpha tocopherols, such as vitamin E acetate, ascorbic acid, butylated hydroxyanisole, and butylated hydroxytoluene); polar solvents (e.g., water, propylene glycol, and glycerin); hydrophobic solvents (e.g., corn oil, castor oil, soybean oil, olive oil, fish oil, peanut oil, peppermint oil, safflower oil, sesame oil, medium chain triglycerides, caprylic triglycerides, capric triglycerides derived from coconut oil or palm seed oil); and viscosity increasing agents (e.g., gelatin, glycerin, carrageenan, colloidal silicon dioxide, hydrogenated vegetable oil, povidone, and propylene glycol alginate).

E. Dosage Forms

The microparticle compositions described herein are generally formulated for oral or parenteral administration. Suitable oral dosage forms include capsules, such as hard or soft, gelatin or non-gelatin capsules, or oral suspensions or syrups. Suitable parenteral formulations include suspensions.

1. Capsules

In one embodiment, the microparticle compositions (microparticles suspended in a hydrophilic or lipophilic carrier) are encapsulated in a capsule, such as a hard or soft capsule. The capsules can be prepared from natural and/or synthetic film forming polymers. Suitable natural film forming materials include, but are not limited to gelatin. Non-gelatin capsules include, but are not limited to, capsules made from carageenan, shellac, alginates, pectin, and zeins. Suitable synthetic film-forming polymers include, but are not limited to, methyl cellulose, hydroxypropyl methyl cellulose acetate succinate, hydroxypropyl methyl cellulose phthalate, cellulose acetate phthalate, and acrylates such as poly (meth) acrylate.

The compositions can also be encapsulated in an enteric capsule, wherein the capsule is coated with an enteric coating or the capsule shell contains an enteric polymer as described in WO 2004/030658 to Banner Pharmacaps, Inc.

Hard shell capsules are typically prepared by forming the two capsule halves, filling one of the halves with the fill solution, and then sealing the capsule halves together to form the finished capsule. Soft gelatin capsules are typically prepared using a rotary die encapsulation process. Such processes are known in the art.

The capsule shell can contain one or more additives. Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

2. Oral Suspensions

Alternatively, the composition can be administered as an oral suspension, such as a syrup. The solution or suspension may be prepared using one or more pharmaceutically acceptable excipients. Suitable excipients include, but are not limited to, surfactants, humectants, plasticizers, crystallization inhibitors, wetting agents, dispersing agents, pH adjusting agents, flavorants, colorants, and combinations thereof.

III. Methods of Manufacture

A. Microparticles

The microparticles described herein may exhibit improved dissolution and enhance absorption in vivo as compared to formulations containing the active agent suspended in an oil-based (e.g., lecithin and Capmul or polyoxyl 40 stearate and glyceryl monostearate) or aqueous-based carrier. The microparticles can be made by a co-melting process or co-dissolving process. For example, the active agent can be melted, dissolved, or suspended in one or more molten fatty acids, conjugated fatty acids, hydrophilic polymers, and/or surfactants at a temperature dependent on the melting point of the active agent and any coating materials used to form the microparticles. The active agent, coating material(s), and optionally any additives are melted at a temperature typically between about 40° C. and about 75° C., preferably between about 40 and 60° C., in a suitable reactor vessel, such as a medicine tank. A solvent may be used to dissolve or suspend the active agent in the coating material.

The active agent-coating material mixture is added to a lipophilic or hydrophilic carrier, typically at room temperature or less, with vigorous stirring and/or homogenization to form microparticles suspended in the hydrophilic or lipophilic carrier. Alternatively, the hydrophilic or lipophilic carrier can be added to the mixture of drug and coating material(s) and homogenized to form microparticles.

The active agent-coating material mixture and the hydrophilic or lipophilic carrier are stirred for a period of time until the mixture is homogeneous, typically for a period of time less than about 30 minutes, to form the microparticles. In one embodiment, the mixture is stirred for about 10 minutes, preferably about 5 minutes to form microparticles having a diameter from about 100 nm to about 25 microns, preferably about 5 to about 25 microns, more preferably from about 10 to about 25 microns, more preferably from about 10 to about 20 microns. In another embodiment, the microparticles have a diameter less than about 10 microns, less than about 5 microns, less than about 1, less than 0.5 microns, less than 0.25 microns, or less than 0.1 microns. The diameter of the microparticles can be varied by varying the mixing times; generally, the longer the mixing times, the smaller the particle size.

Homogenization processes can also be used to reduce the particle size. Homogenization is a fluid mechanical process that involves the subdivision of particles or droplets into micron sizes to create a stable dispersion or emulsion for further processing. This process occurs when the fluid passes through a minute gap in the homogenizing valve. This creates conditions of high turbulence and shear, combined with compression, acceleration, pressure drop, and impact, causing the disintegration of particles and dispersion throughout the product. After homogenization, the particles are of a uniform size, depending on the operating pressure and the time of homogenization.

B. Encapsulation of the Microparticles

The microparticles, alone or suspended in the hydrophilic or lipophilic carrier mixture, can be encapsulated in hard or soft capsules. The capsules can be gelatin capsules or non-gelatin capsules (e.g., carageenan, starch, polysaccharides, etc.). Encapsulation can occur at room temperature or at elevated temperatures (up to 35° C. for soft gelatin capsules and up to 60° C. for non-animal soft shell capsules) to facilitate the fill flow. Encapsulation in soft shell capsules may be done using a rotary die encapsulation machine using standard procedures. The capsules are dried to the desired hardness and/or fill moisture content to facilitate the handling of the capsules during packaging, shipping, and storage. The fill weight range of the finished capsules is typically from 100 mg to 2200 mg in a capsule suitably sized for swallowing. The capsules are processed following standard procedures and can be packaged in either bottles or blisters packs. The capsules may be coated with one or more delayed release, extended release, or enteric materials. Alternatively, the microparticles can be incorporated into an enteric capsule, wherein the enteric polymer is contained in the capsule shell, as described in WO 2004/030658 to Banner Pharmacaps, Inc.

IV. Methods of Use

The compositions described herein can be used to administer an active agent to a patient in need thereof. The amount of active agent to be administered can be readily determined by one of ordinary skill in the art and is dependent on several factors, including the disease or disorder to be treated and the age and weight of the patient. Specifically, the compositions described herein can be used to administer poorly insoluble and/or poorly absorbable active agents. The compositions described herein can enhance dissolution and/or bioavailability of the active agent.

The dissolution performance of the compositions described herein depends, at least in part, on the HLB of the surfactant and/or modified fatty acid. Hydrophobic drugs of low aqueous solubility present poor dissolution characteristics. To improve drug dissolution, the physical characteristics of the drug can be modified to increase effective surface area. The use of high HLB surfactants as formulation adjuvants may improve the drug dissolution by enhancing wetting and micellar solubilization in presence of water or polar solvents. Further, absorption of the active agent may be enhanced due to the fatty acid coating on the microparticles.

Microparticles containing a water-insoluble drug coated with a conjugated fatty acid suspended in a hydrophilic carrier exhibit faster dissolution rates than aqueous or oil-based suspensions of the drug. For example, in vitro release studies of formulations containing fatty acid-coated fenofibrate microparticles showed approximately 85% dissolution of fenofibrate in 15 minutes and approximately 100% dissolution in 60 minutes, which is significantly faster than fenofibrate suspended in an aqueous carrier. Under fasting conditions, the fenofibrate concentration in vivo was more than twice the concentration of fenofibrate suspended in water. Under non-fasting conditions, absorption of fenofibrate from fatty acid coated drug particles was substantially higher than for fenofibrate suspended in water. Fenofibrate absorption of fatty acid-coated microparticles was comparable under non-fasting and high fat conditions.

In another embodiment, in vitro release studies of formulations containing cilostazol showed 100% dissolution of cilostazol in 15 minutes, which is significantly faster than cilostazol suspended in an oil-based carrier containing lecithin and Capmul (CLZ-02) and cilostazol in tablet form suspended in water (Pletal®). The same formulation showed greater absorption in vivo compared to the aqueous and oil-based suspensions under fed and fasting conditions. For example, the compositions described herein exhibited an almost 400% increased in the $AUC_{0-24}$ under fasting condition compared to Pletal® and an almost 100% increase in the $AUC_{0-24}$ compared to cilostazol suspended in an oil-based carrier containing lecithin and Capmul.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

Preparation of Fatty Acid Coated Fenofibrate Particles

Microparticles containing a fatty acid and fenofibrate were prepared. Glyceryl monostearate was melted at 70° C. with mixing. Fenofibrate was added slowly to the molten glyceryl monostearate with stirring. The mixture was maintained at 70° C. and the hydrophilic carrier was added slowly with mixing at 350 rpm until the mixture was homogeneous. The mixture was cooled to 30° C. Following cooling, the mixture was homogenized until an aggregate-free suspension was obtained.

The composition of the drug and coating material mixture and the hydrophilic phase used to form the microparticles is shown in Table 1.

TABLE 1

Composition of the drug and coating material mixture and hydrophilic phase

| Drug and Coating Material Mixture | Weight % of composition | g/Batch |
| --- | --- | --- |
| Polyoxy 40 stearate or Glyceryl monostearate | 10.5 | 10.5 |
| Fenofibrate | 14.5 | 14.5 |
| Sub total | 25.0 | 25.0 |

| Hydrophilic phase | % | g/Batch |
| --- | --- | --- |
| PEG 400 | 57.0 | 57.0 |
| Water | 8.0 | 8.0 |
| Tween 20 | 10.0 | 10.0 |
| Sub total | 75.0 | 75.0 |
| Total | 100.0 | 100.0 |

Example 2

In Vitro Release Profiles of Fatty Acid Coated Fenofibrate Particles

Figure 1A:
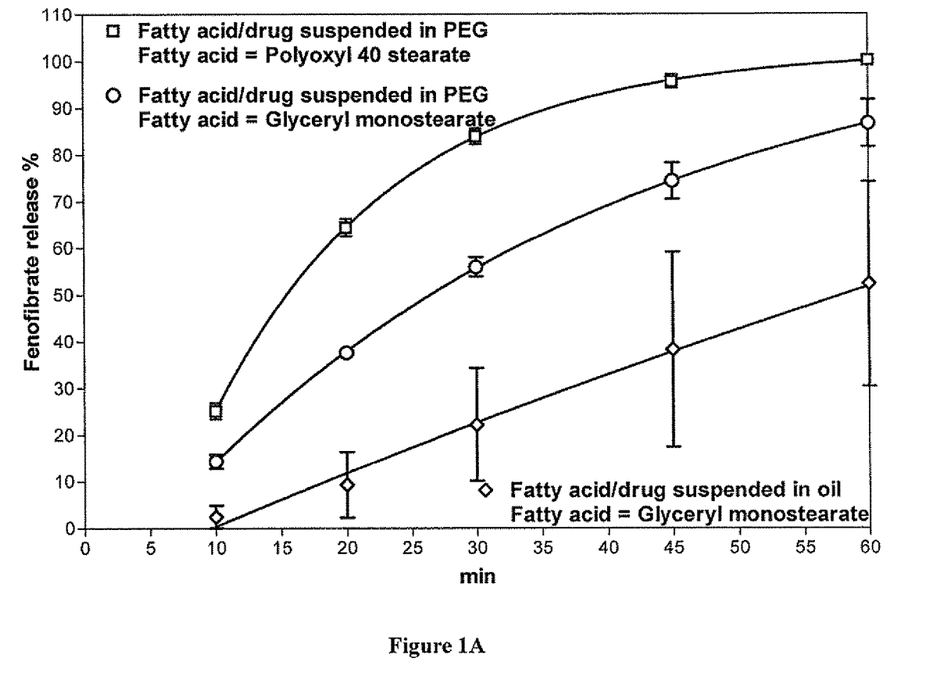
FIG. 1A is a graph showing the dissolution profile in vitro for microparticles containing fenofibrate (% fenofibrate released) and a fatty acid (polyoxyl 40 stearate (□) and glyceryl monostearate, (○)) suspended in polyethylene glycol (PEG) as a function of time (minutes) compared to fenofibrate and fatty acid suspended in polyoxyl 40 stearate and glyceryl monostearate (◊).

In vitro drug release studies were conducted using a USP dissolution apparatus II (paddles) at 75 rpm. Experiments were conducted in dissolution media at 37.0±0.5° C. in 1000 mL of 0.05 M sodium dodecyl sulfate. Samples were withdrawn and analyzed via HPLC having at UV detector. The detection wavelength was 286 nm. The results are shown in FIG. 1A. In vitro release studies of formulations containing fenofibrate showed approximately 85% dissolution of fenofibrate in 15 minutes and approximately 100% dissolution in 60 minutes, which is significantly faster than fenofibrate suspended in an oil-based carrier.

Example 3

Preparation of Fatty Acid Coated Cilostazol Particles

Particles containing cilostazol (14.5% by weight) were prepared using the procedure and materials described above. The microparticles were formed by combining a mixture of glycerin ester of behenate (8.49% w/w), vitamin E acetate (8.49% w/w), sorbitan monostearate (Span 80, 1.00% w/w) and cilostazol with a hydrophilic carrier containing polyethylene glycol (54.74% w/w), water (8.43% w/w), Cremophor RH 40 (1/89% w/w), and Tween 20 (3.78% w/w). The mixture was homogenized using Ultra-Torrax followed by deaeration. The homogenized fatty acid suspension was passed through Ultra-Torrax three times to reduce the particle size distribution (<500 nm).

Example 4

In Vitro and In Vivo Release Profiles of Fatty Acid Coated Cilostazol Particles

Figure 1B:
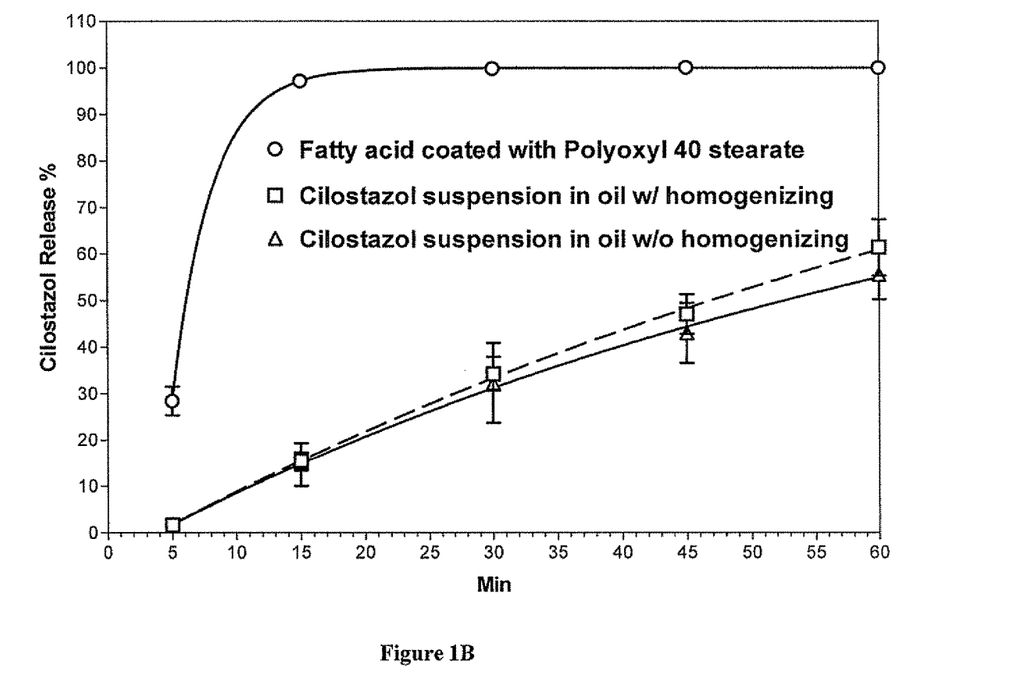
FIG. 1B is a graph showing the dissolution profile in vitro for microparticles containing cilostazol (% cilostazol released) and a fatty acid conjugate (glyceryl ester of behenate, sold as Compritol 888 ATO and available from Gattfosse, Saint-Priest, France) (◊) coated with polyoxyl 40 stearate as a function of time (minutes) with (□) and without (Δ) homogenization compared to cilostazol suspensions in lecithin and Capmul.

In vitro drug release studies were conducted using a USP dissolution apparatus II (paddles) at 75 rpm. Experiments were conducted in dissolution media at 37.0±0.5° C. in 1000 mL of 0.05 M sodium dodecyl sulfate. Samples were withdrawn and analyzed via HPLC having at UV detector. The detection wavelength was 286 nm. The results are shown in FIG. 1B. In vitro release studies of formulations containing cilostazol showed 100% dissolution of cilostazol in 15 minutes, which is significantly faster than cilostazol suspended in an oil-based carrier containing lecithin and Capmul (CLZ-02) and cilostazol in tablet form suspended in water (Pletal®).

Figure 2A:
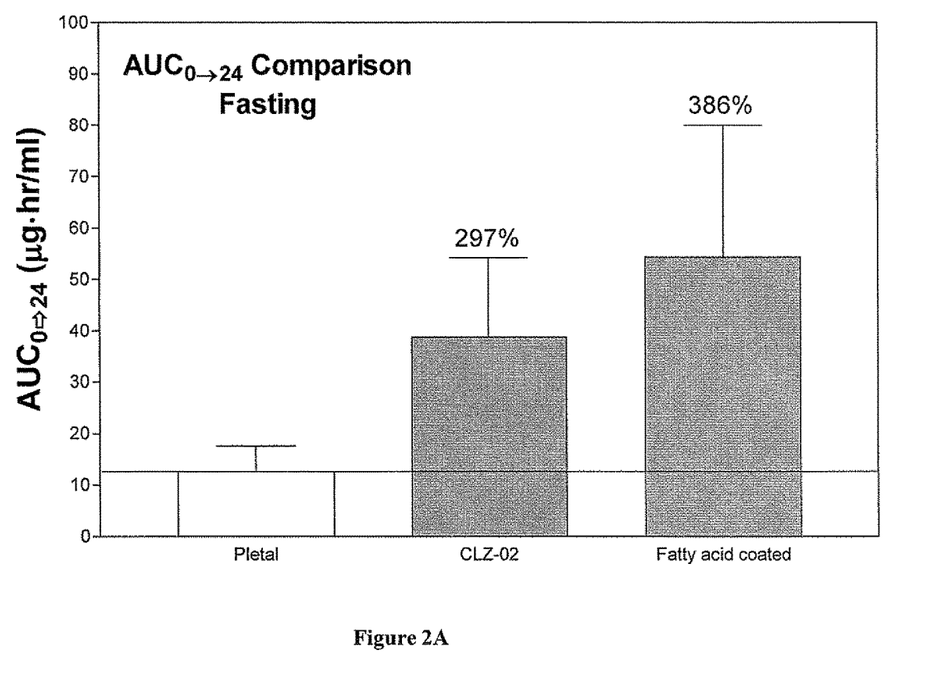
FIG. 2A is a graph showing the enhanced absorption in vivo under fasting conditions for glycerin ester of behenate-coated cilostazol nanoparticles compared to Pletal® (cilostazol in tablet form, suspended in water) and cilostazol suspended in an oil-based carrier containing lecithin and Capmul (CLZ-02).
Figure 2B:
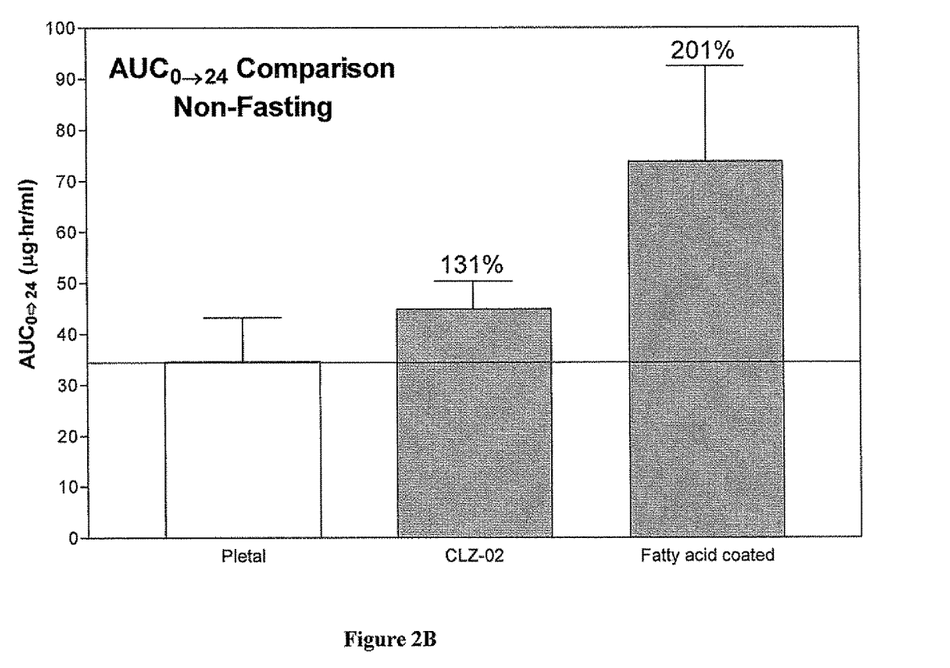
FIG. 2B is a graph showing the enhanced absorption in vivo under fed conditions for glycerin ester of behenate-coated cilostazol nanoparticles versus Pletal® (cilostazol in tablet form) and CLZ-02.

FIG. 2 shows the absorption of various cilostazol formulations under fed and fast conditions. FIG. 2A shows the enhanced absorption in vivo under fasting conditions for glycerin ester of behenate-coated cilostazol nanoparticles compared to Pletal® (cilostazol in tablet form, suspended in water) and cilostazol suspended in an oil-based carrier containing lecithin and Capmul (CLZ-02). FIG. 2B shows the enhanced absorption in vivo under fed conditions for glycerin ester of behenate-coated cilostazol nanoparticles versus Pletal® (cilostazol in tablet form) and CLZ-02.

Example 5

In Vitro and In Vivo Release Profiles of Fatty Acid Coated Fenofibrate Particles Fatty acid-coated particles of fenofibrate were prepared using a procedure similar to the procedure described in Example 1. The drug-coating material mixture contained glyceryl ester of behenate (4.25% w/w), stearoyl macrogol glyceride (sold under the tradename Gelucire 50/13 and available from Gattefosee, 4.25% w/w), soybean oil (8.49% w/w), sorbitan monostearate (Span 80, 1.89% w/w), and fenofibrate (15.08% w/w). The fenofibrate was co-melted with the fatty acid mixture and spread onto aluminum foil to allow it to cool. 33.96% of the fenofibrate/fatty acid mixture was added to a hydrophilic carrier containing polyethylene glycol (54.74% w/w), water (7.54%, w/w), Cremophor RH 49 (1.89% w/w), and Tween 20 (1.89% w/w). The mixture was homogenized using Ultra-Torrax for five minutes followed by deaeration. The homogenized fatty acid suspension was passed through the Ultra-Torrax three times to reduce the particle size distribution (<500 nm).

A comparative study was conducted using two formulations: (1) a fenofibrate suspension in aqueous solution and (2) fenofibrate/lipid particles suspended in PEG 400. The in vivo absorption was in rats was measured as described below.

Two formulations containing 20.0 mg fenofibrate/200 μL were administered to two different group of rats (n=6) via oral gavage. For the non-fasting experiments, each group of rats was given a normal diet ad libitum. For the fasting experiments, food was prohibited for 12 hours prior to dosing and provided again 2 hours post-administration. Another group was treated with a high fat meal containing 25% (W/W) peanut butter. For all groups water was provided ad libitum. Blood samples were collected at 0, 0.5, 1.0, 2.0, 3.0, 4.0, 6.0, 8.0, 10.0, 12.0 and 24.0 hours post administration and immediately centrifuged at 10,000 RPM for 10 min to obtain plasma samples.

Plasma samples were vortexed with n-hexane/ethylacetate (90/10 v/v) and centrifuged at 10,000 RPM for 4 min. The organic layer was separated and dried at 40° C. under vacuum overnight. The residue was reconstituted with acetonitrile and analyzed by HPLC. HPLC was done using a phenol column (4.6×250 mm, 5 μM) at 25° C. using a UV detector (286 nm). The mobile phase was acetonitrile/0.02M phosphoric acid mixture. The results are shown in FIG. 3.

Figure 3A:
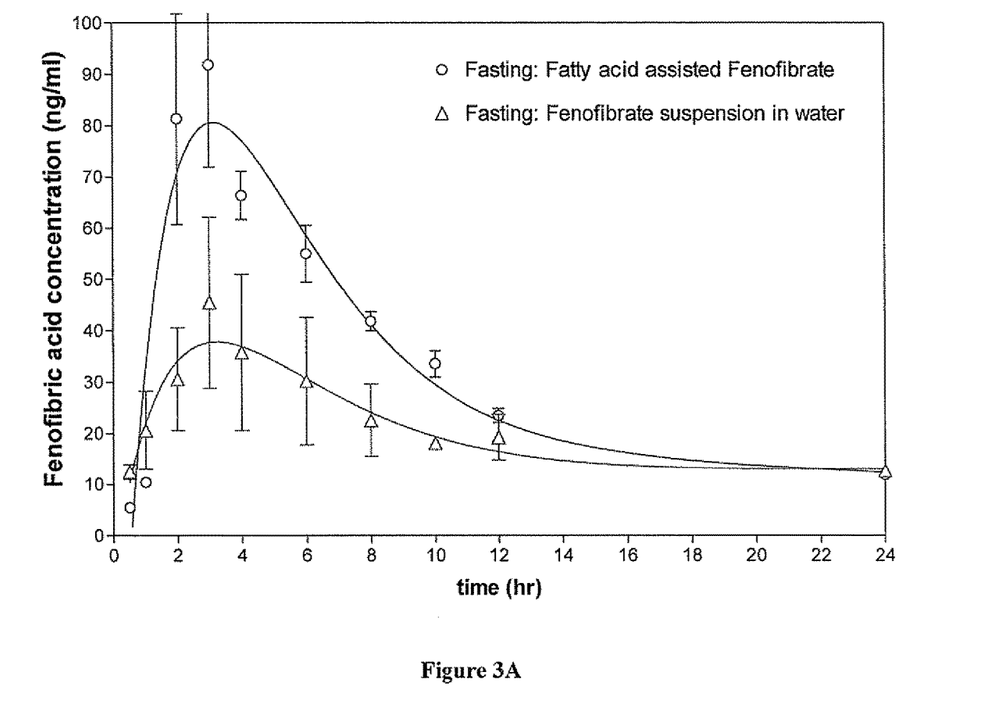
FIG. 3A is a graph showing the difference in absorption of fenofibrate (fenofibric acid, ng/mL) as a function of time (hours) for fatty acid-coated fenofibrate (○) and fenofibrate suspended in water (Δ) under fasting conditions.

FIG. 3 is a graph showing the absorption of various fenofibrate formulations as a function of time. FIG. 3A is a graph showing the difference in absorption of fenofibrate (fenofibric acid, ng/mL) as a function of time (hours) for fatty acid-coated fenofibrate (○) and fenofibrate suspended in water (Δ) under fasting conditions. Absorption of fenofibrate in vivo was improved more than two fold compared to the suspension of fenofibrate in water.

Figure 3B:
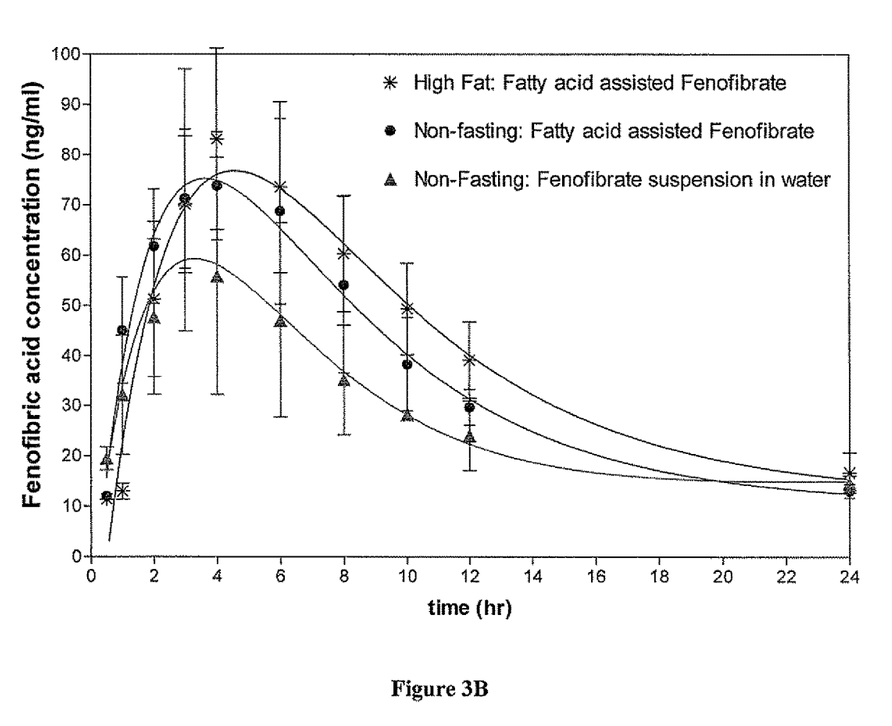
FIG. 3B is a graph showing the difference in absorption of fenofibrate (fenofibric acid, ng/mL) as a function of time (hours) for fatty acid-coated fenofibrate (♦) and fenofibrate suspended in water (▲) under non-fasting conditions and fatty acid-coated fenofibrate taken after a high fat meal (*).

FIG. 3B is a graph showing the difference in absorption of fenofibrate (fenofibric acid, ng/mL) as a function of time (hours) for fatty acid-coated fenofibrate (♦) and fenofibrate suspended in water (▲) under non-fasting conditions and fatty acid-coated fenofibrate taken after a high fat meal (*). Absorption of fenofibrate from fatty acid coated drug particles was substantially higher than for fenofibrate suspended in water. Fenofibrate absorption of fatty acid-coated microparticles was comparable under non-fasting and high fat conditions. $T_{max}$ under high fat conditions was slightly longer than under non-fasting conditions.

Figure 4:
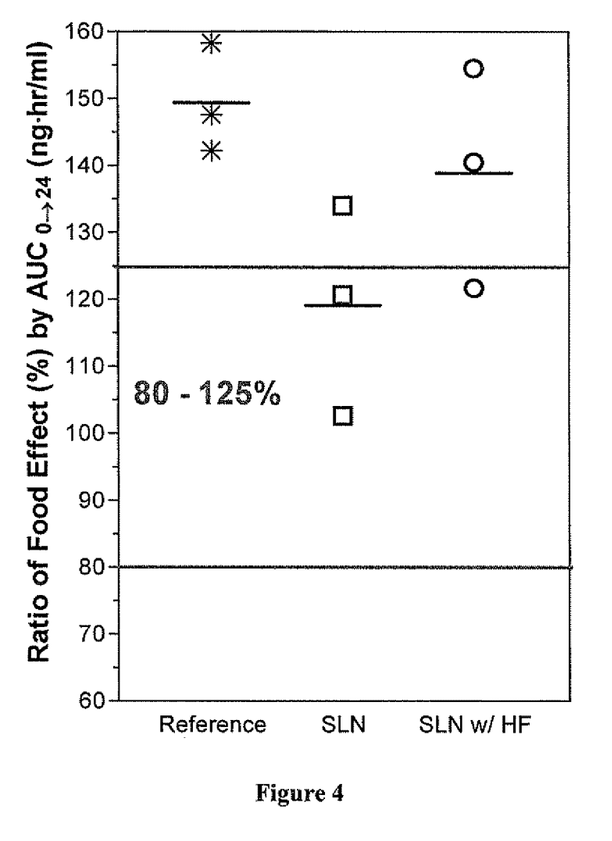
FIG. 4 is a graph showing the food effect on the absorption of three fenofibrate formulations: a reference formulation (described in Example 3); solid lipid nanoparticles (SLN); and solid lipid nanoparticles with high fat (SLN HF), as a function of the formulation.

FIG. 4 is a graph showing the food effect in rats on the absorption of three fenofibrate formulations: fatty acid coated fenofibrate particles (reference); solid lipid nanoparticles (SLN); and solid lipid nanoparticles with high fat, as a function of the formulation. The fatty acid-coated fenofibrate particles suspended in NaCl solution showed a food effect with normal diet: the high (158%) and low (142%) end of $AUC_{0-24}$ were outside 80 to 125% of the equivalent range compared to fasting conditions. The fill formula containing solid lipid nanoparticles included the median (120%) and lower end (103%) of $AUC_{0-24}$ within 80 to 125% of the equivalent range. Under high fat meal conditions (meal containing 25% (w/w) of peanut butter), the solid lipid nanoparticles formulation exhibited a more pronounced food effect than under normal diet (122% to 155% of the ratio of food effect by $AUC_{0-24}$). This observation suggests that 25% (w/w) of a high fat diet (e.g., peanut butter) in normal rodent diet could enhance the absorption of fenofibrate.

We claim:

1. A method of making microparticles comprising:
    (a) dissolving, melting, or suspending fenofibrate or cilostazol in at least one fatty acid or conjugated fatty acid, surfactant, hydrophilic polymer, or combinations thereof to form a mixture, and
    (b) mixing the mixture of step (a) with a liquid hydrophilic or lipophilic carrier to form microparticles having a diameter from 100 nm to 25 microns.

2. The method of claim 1, wherein the surfactant in step (a) has an HLB greater than about 10.

3. The method of claim 2, wherein the surfactant in step (a) has an HLB greater than about 16.

4. The method of claim 1, wherein the concentration of the surfactant is from about 1% to about 50% by weight of the composition.

5. The method of claim 4, wherein the concentration of the surfactant is from about 5% to about 15% by weight of the composition.

6. The method of claim 1, wherein the conjugated fatty acid is selected from the group consisting of $C_{10}$-$C_{18}$ monoglycerides, $C_{10}$-$C_{18}$ fatty acids conjugated to a polyalkylene oxide, $C_{10}$-$C_{18}$ fatty acids conjugated to a monosaccharide, and combinations thereof.

7. The method of claim 1, wherein the concentration of the conjugated fatty acid is from about 1% to about 20% by weight of the composition.

8. The method of claim 1, wherein the concentration of the conjugated fatty acid is from about 5% to about 15% by weight of the composition.

9. The method of claim 1, wherein the fatty acid is a $C_{10}$-$C_{18}$ fatty acid.

10. The method of claim 1, wherein the fatty acid is selected from the group consisting of dodecanoic (lauric) acid, tetradecanoic (myristic) acid, hexadecanoic (palmitic) acid, heptadecanoic (margaric) acid, octadecanoic (stearic) acid, eicosanoic (arachidic) acid, docosanoic (behenic) acid, tetracosanoic (lignoceric) acid, hexacosanoic (cerotic) acid, heptacosanoic (carboceric) acid, octacosanoic (montanic) acid, triacontanoic (melissic) acid, dotriacontanoic (lacceroic) acid, tritriacontanoic (ceromelissic) acid, tetratriacontanoic (geddic) acid, pentatriacontanoic (ceroplastic) acid, and combinations thereof.

11. The method of claim 1, wherein the concentration of the fatty acid is from about 1% to about 20% by weight of the composition.

12. The method of claim 1, wherein the concentration of the fatty acid is from about 5% to about 15% by weight of the composition.

13. The method of claim 1, wherein the hydrophilic polymer is selected from the group consisting of poloxomers, poloxamines, and polyethylene glycols.

14. The method of claim 1, wherein the concentration of the hydrophilic polymer is from about 1% to about 80% by weight of the composition.

15. The method of claim 14, wherein the concentration of the hydrophilic polymer is from about 30% to about 60% by weight of the composition.

16. The method of claim 14, wherein the concentration of the hydrophilic polymer is from about 5% to about 15% by weight of the composition.

17. The method of claim 1, wherein the water-insoluble active agent is melted, dissolved or dispersed in the coating material at a temperature between about 40° C. and about 70° C.

18. The method of claim 1, wherein the mixture of step (a) is added to the hydrophilic or lipophilic carrier at room temperature or lower.

19. The method of claim 1, wherein the mixture of step (a) is suspended and homogenized in a hydrophilic or lipophilic carrier to form the microparticles.

20. The method of claim 19, wherein the mixture of step (a) and the hydrophilic or lipophilic carrier is homogenized for less than about 30 minutes.

21. The method of claim 1, wherein the hydrophilic carrier comprises polyethylene glycol, water, and one or more surfactants.

* * * * *